US00PP30000P3

(12) United States Plant Patent
Hansen

(10) Patent No.: US PP30,000 P3
(45) Date of Patent: Dec. 18, 2018

(54) ***HOSTA* PLANT NAMED 'ONE LAST DANCE'**

(50) Latin Name: ***Hosta* hybrid (Tratt.)**
Varietal Denomination: One Last Dance

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 55 days.

(21) Appl. No.: 15/530,300

(22) Filed: Dec. 20, 2016

(65) Prior Publication Data

US 2018/0177098 P1 Jun. 21, 2018

(51) Int. Cl.
*A01H 5/12* (2018.01)
*A01H 5/02* (2018.01)

(52) U.S. Cl.
USPC ..... Plt./353
CPC ..... *A01H 5/02* (2013.01); *A01H 5/12* (2013.01)

(58) Field of Classification Search
USPC ..... Plt./353
CPC ..... A01H 5/02; A01H 5/0272; A01H 5/12; A01H 5/00; A01H 6/56
See application file for complete search history.

(56) References Cited

PUBLICATIONS

Commonwealth Nurseries 2016 ProNur Perennial Availability, retrieved on Jan. 18, 2018, retrieved from the Internet at http://www.comnur.com/pronur_availabilty3.htm, pp. 1-4 (Year: 2016).*

* cited by examiner

*Primary Examiner* — June Hwu

(57) ABSTRACT

A new and distinct *Hosta* plant named 'One Last Dance' with large rounded-mound habit of dense variegated foliage having blades of wide, intense, yellow margins developing to light yellow, and dark center with long, irregular, intermediate feathering colors. The plant produces large, soft lavender flowers in mid-summer on tall, slightly arching scapes well above the leaves with deeply impressed veins and wavy margins.

2 Drawing Sheets

Latin name and variety denomination of the plant:
Botanical classification: *Hosta* hybrid (Tratt.).
Variety denomination: 'One Last Dance'.

FEDERALLY SPONSORED RESEARCH

This invention was developed without any federally sponsored research or development funding.

BACKGROUND AND ORIGIN OF THE PLANT

The present invention relates to a new and distinct *hosta* plant, *Hosta* 'One Last Dance' hereinafter also referred to as the new plant or just the cultivar name, 'One Last Dance'. *Hosta* 'One Last Dance' was discovered by the inventor as a non-induced, naturally-occurring, whole-plant, chimeral mutation in a batch of tissue culture propagated *Hosta* 'Dancing Queen' (not patented) at a wholesale nursery greenhouse in Zeeland, Mich., USA in the summer of 2011. The new plant has been asexually propagated by division at the same nursery in Zeeland, Mich., USA since 2014 and also by careful plant shoot tip tissue culture with the resultant asexually propagated plants having retained all the same traits as the original plant. *Hosta* 'One Last Dance' is stable and reproduces true to type in successive generations of asexual reproduction.

No plants of *Hosta* 'One Last Dance' have been sold, under this or any other name, in this country or anywhere in the world, prior to the filing of this application, nor has any disclosure of the new plant been made prior to the filing of this application with the exception of that which may have been disclosed within one year of the filing date of this application and was either derived directly or indirectly from the inventor.

BRIEF SUMMARY OF THE PLANT

There are over 5,600 registered *hosta* cultivars with The American *Hosta* Society, which is the International Cultivar Registration Authority for the genus *Hosta* along with a similar number of unregistered cultivars. The nearest comparison variety is *Hosta* 'American Icon' U.S. Plant Pat. No. 17,441, and the new plant differs by having larger habit, taller scapes with larger and more flowers and larger foliage but similar variegation pattern, colors and rippling or sinuate margins.

Other similar *hostas* include: 'American Choo Choo' (not patented), 'Satisfaction' (not patented) and 'Sentimental Journey' (not patented). Compared with 'American Choo Choo' the new plant is larger in leaf, scape and habit and has more sinuate leaf margins. Compared with 'Satisfaction' the new plant has less broad variegated margins and larger more sinuate leaves. Compared with 'Sentimental Journey' the new plant has greater contrasting yellow leaf margin and dark green center and the margin is not as sinuate compared with the chartreuse leaf margin and medium green center of 'Sentimental Journey'. 'Tyler's Treasure' (not patented) develops a more yellowish-cream leaf margin and does not have the sinuate leaf margin.

Other *Hosta* cultivars have variegated foliage, but 'One Last Dance' is distinct from the above mentioned *hostas* and all other cultivars known to the discoverer by the following combined traits:

1. Large rounded-mound plant habit with dense variegated foliage;
2. Foliage with wide, intense, yellow margins developing into a light yellow margin, dark green centers and long, intermediate, streaks of colors between;
3. Soft lavender flowers on tall slightly arching scapes; and
4. Leaves with deeply impressed veins above and deep sinuate undulation in margins.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

FIG. 3 shows a close-up of the foliage from a five-year-old plant in mid- to late summer with light yellow margins, dark green center and several intermediate streaks of different colors between.

DETAILED BOTANICAL DESCRIPTION

Figure 1:
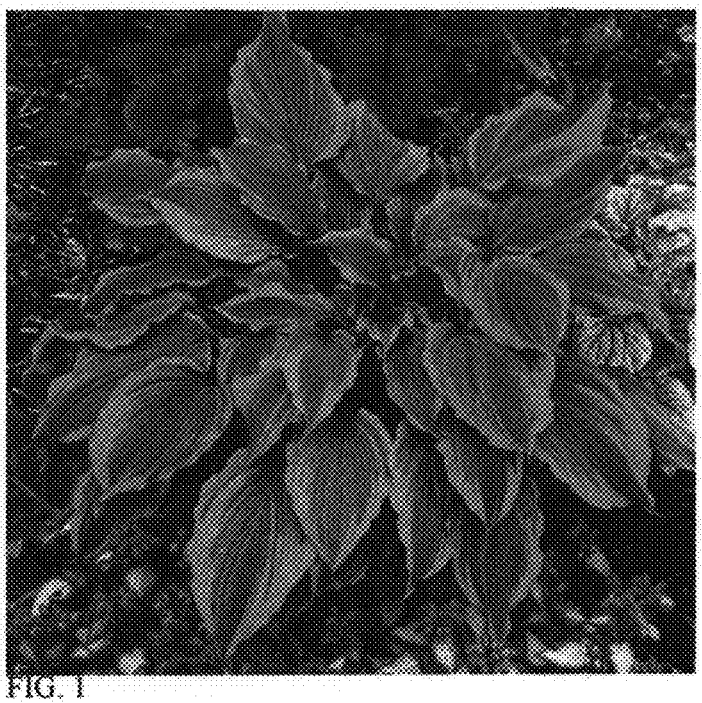
FIG. 1 shows a three-year-old plant grown in a shaded greenhouse with early summer foliage.
Figure 2:
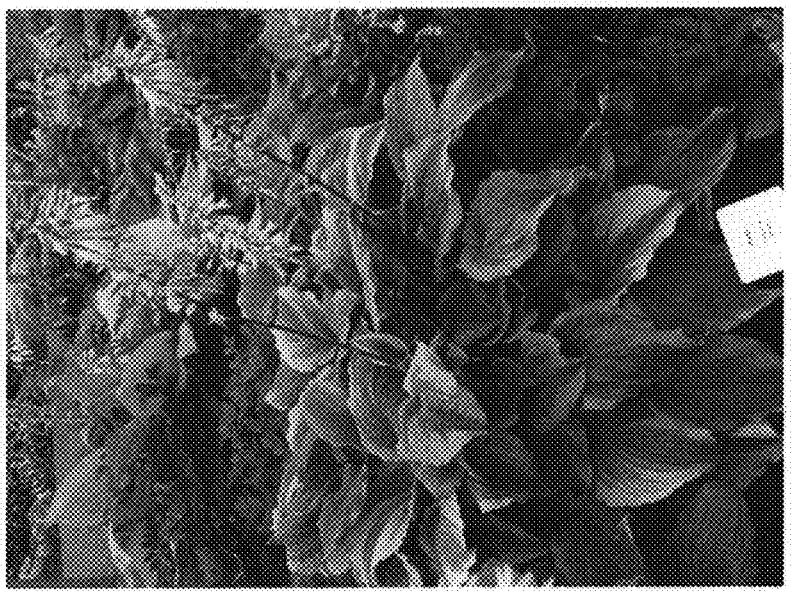
FIG. 2 shows a five-year-old plant in full-flower in a shaded trial garden at a nursery in Zeeland, Mich. with supplement fertilizer and water as needed.
Figure 3:
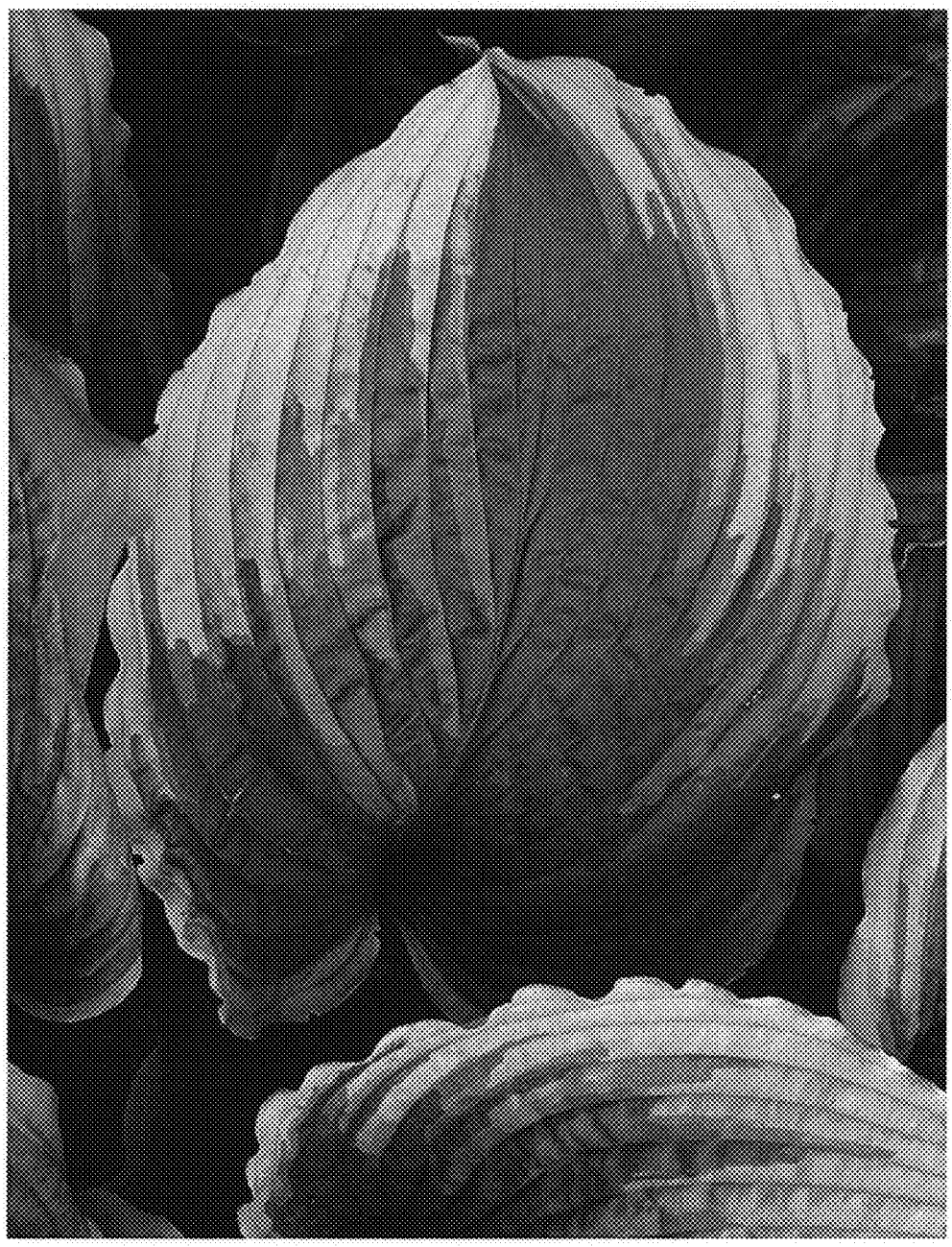

The following descriptions and color references are based on the 2001 edition of The Royal Horticultural Society Colour Chart except where common dictionary terms are used. The new plant, *Hosta* 'One Last Dance', has not been observed under all possible environments. The phenotype may vary slightly with different environmental conditions, such as temperature, light, fertility, moisture and maturity levels, but without any change in the genotype. The following observations and size descriptions are of a potted three-year old plant in a shaded greenhouse in Zeeland, Mich. with supplemental water and fertilizer.

Botanical classification: *Hosta* hybrid;

Parentage: Whole-plant mutation of *Hosta* 'Dancing Queen' (not patented);

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching;

Plant shape and habit: Hardy herbaceous perennial with basal rosette of leaves emerging from rhizomes producing a large symmetrical rounded-mound of leaves;

Plant size: Foliage height about 80.0 cm above soil line to the top of the leaves and about 145.0 cm wide at the widest point slightly above the soil line;

Foliage description: Glabrous, slightly glaucous abaxial and slightly lustrous adaxial; cordate; margin entire and sinuate; acute apex with cordate base;

Leaf blade size: To about 35.0 cm long and 23.5 cm wide with margin about 7.0 cm wide, average about 28.0 cm long and 20.0 cm wide with margin about 5.5 cm wide;

Leaf blade color: Early season and shortly after emerging adaxial center color blend between RHS 137A and RHS 138A, margin blend between RHS N144A and RHS 145A, irregular intermediate streaks and patches consisting of nearest RHS N138D, RHS N138C and RHS 143C; early season abaxial center nearest RHS 143A, early season abaxial margin nearest RHS 151D; other intermediate colors in irregular patches and stripes between the margin and center comprising nearest RHS 145A and RHS N144D; mid-season and later summer adaxial centers nearest RHS 137A, mid-season and later adaxial margins varying between RHS 18B and RHS 146C depending on light intensity; mid-season and later abaxial center between RHS 137B and RHS 138A, mid-season and later abaxial margins nearest RHS N144A, other intermediate colors in irregular stripes and patches comprising nearest RHS N144C and RHS 145A;

Petiole: Entire, glabrous, concavo-convex; slightly arching from base of plant to leaf base, stiff; to about 50.0 cm long and at base 3.5 cm across and 2.5 cm deep; average 46.0 cm long and base 2.5 mm wide and 1.5 cm deep;

Petiole color: Adaxial midrib between RHS 143C and RHS 137D with margin nearest RHS 144A; abaxial midrib nearest RHS 145D with margin nearest RHS 144A and center blending to nearest RHS 137C before margin;

Veins: Parallel, camptodrome; deeply impressed adaxial, costate and asperous abaxial; 14 to 16 pairs with one midrib, average 15 pairs;

Veins color: Adaxial nearest RHS 147C and abaxial nearest RHS 148C;

Flower description:

Buds one day prior to opening: Clavate with rounded apex and narrow tubular base; about 57.0 mm long, apical bulb about 12.5 mm diameter and tube about 4.0 mm diameter;

Bud color: Nearest RHS N80D;

Inflorescence: Average flowering portion 35.0 cm long and 8.0 cm wide;

Flowers: perfect: Single; campanulate, funnelform; actinomorphic; attitude drooping; about 3.6 cm wide and 6.4 cm long, fused tube portion about 1.8 cm long and 4.5 mm diameter (distal flowers smaller); persistent; effective for a normal period, usually one day on plant or as cut flower; scapes remain effective with flowers beginning early summer for about three weeks; about 60 flowers per scape; average spacing between flowers about 0.5 cm, significantly greater in proximal flowers;

Floral bracts: Lanceolate; acute apex; truncate sessile base; concavo-convex; to about 8.5 cm long and 2.5 cm wide decreasing distally, average about 2.8 cm long and 9.0 mm across;

Floral bract color: Nearest RHS 145D with light blush of nearest N77D;

Flower fragrance: None detected;

Tepal: Six; two nearly identical sets of three, glabrous, entire; with acute apex; inner set with transparent margin about 1.0 mm wide; approximately 4.5 cm long and about 1.0 cm wide;

Tepal color: Coloring of both sets adaxial longitudinal center about 4.0 mm wide nearest RHS N80D and longitudinal edge lighter than RHS 76D without obvious veins; abaxial between RHS 76C and RHS 76D; abaxial tube between RHS 76C and RHS 76D;

Gynoecium: Single; tri-carpelled;

*Style*.—Single, approximately 6.2 cm long, 1.0 mm diameter, curved upward about 90° in distal 2.0 cm; color lighter than RHS 155D.

*Stigma*.—Globose, about 1.5 mm in diameter; color nearest RHS 155D.

*Ovary*.—Oblong, about 7.0 mm long and 2.5 mm diameter at widest; rounded apex and truncate base; color nearest RHS 155A.

Androecium:

*Filaments*.—Six, approximately 5.5 cm long and 0.8 mm in diameter; curved upward in the apical 12.0 mm; color nearest RHS 155D.

*Anthers*.—Elliptic; dorsifixed, longitudinally dehiscent; about 6.0 mm long and 0.5 mm wide; color nearest RHS 177A.

*Pollen*.—Abundant; elliptic, less than 0.1 mm long; color nearest RHS 23A.

Peduncle: Usually one per mature division; glaucous, glabrous to becoming slightly lustrous later in season; upright to slightly arching; about 135.0 cm tall, and up to about 13.0 mm in diameter at base; average about 120.0 cm tall and about 12.0 mm diameter at base;

Peduncle color: When flowering between RHS 137A and RHS 146A;

Pedicel: Glabrous; terete; secund; up to 30.0 mm long and 3.0 mm diameter, average about 14.0 mm long and 2.0 mm diameter; attitude outwardly to slightly drooping; color nearest RHS 146D;

Fruit: Tri-valved dehiscent capsule; elliptic, about 3.4 cm long and 7.0 mm diameter, with thin beak about 0.5 mm diameter extending about 3.5 mm; color as maturing between RHS 137A and RHS 146A and when mature nearest RHS 161B;

Seed: Typically about 30 per capsule; endospermic; flattened-elliptic wing surrounding embryo situated toward one end of ellipse; up to 11.0 mm long and 4.0 mm wide and 1.0 mm thick at embryo; color nearest RHS 202A;

Disease tolerance and resistance: The new plant has not shown any resistance to pests and diseases common to *hostas*. The plant grows best and shows best coloration with plenty of moisture, adequate drainage and light shade, but is able to tolerate some drought when mature. Hardiness at least from USDA zone 3 through 9, and other disease resistance is typical of that of other *hostas*.

It is claimed:

1. A new and distinct ornamental plant cultivar named *Hosta* 'One Last Dance' as herein described and illustrated.

* * * * *